United States Patent [19]

Kiser et al.

[11] Patent Number: 5,719,034
[45] Date of Patent: Feb. 17, 1998

[54] CHEMICAL TIMER FOR A VISUAL TEST STRIP

[75] Inventors: Ernest J. Kiser, Los Altos; Michael F. Tomasco, Cupertino; Edward G. Rice, Palo Alto; Yeung S. Yu, Pleasanton, all of Calif.

[73] Assignee: Lifescan, Inc., Milpitas, Calif.

[21] Appl. No.: 706,753

[22] Filed: Sep. 3, 1996

Related U.S. Application Data

[63] Continuation-in-part of Ser. No. 411,238, Mar. 27, 1995, abandoned.

[51] Int. Cl.$^6$ .............................. C12Q 1/54; C12Q 1/28; G01N 21/00
[52] U.S. Cl. .............................. 435/14; 435/69.2; 422/57; 436/170
[58] Field of Search .............................. 435/4, 14, 25, 435/28, 69.2, 184; 422/57, 101; 436/904, 166, 169, 170

[56] References Cited

U.S. PATENT DOCUMENTS

| | | | |
|---|---|---|---|
| 3,552,928 | 1/1971 | Fetter | 23/253 |
| 3,964,871 | 6/1976 | Hochstrasser | 23/253 |
| 4,649,121 | 3/1987 | Ismail et al. | 436/14 |
| 4,994,238 | 2/1991 | Daffern et al. | 422/56 |
| 5,306,000 | 4/1994 | Palmer et al. | 435/26 |
| 5,306,623 | 4/1994 | Kiser et al. | 435/14 |
| 5,453,360 | 9/1995 | Yu | 435/28 |

FOREIGN PATENT DOCUMENTS

| | | |
|---|---|---|
| 0 317 070 A2 | 5/1989 | European Pat. Off. . |
| 0 574 134 A2 | 12/1993 | European Pat. Off. . |

OTHER PUBLICATIONS

Authors: Rodric H. White–Stevens and Lon R. Stover Title: Interference by Ascorbic Acid in Test Systems Involving Peroxidase II. Redox–Coupled Indicator Systems Publication: Clinical Chemistry, vol. 28, No. 4, 1982, pp. 589–595.

Reaction of Monosaccharides with Proteins: Possible Evolutionary Significance. Science, vol. 213, 10 Jul. 1981.

*Primary Examiner*—Ralph Gitomer
*Attorney, Agent, or Firm*—James Riesenfeld

[57] ABSTRACT

A chemical timer for a direct-reading reagent test strip changes color a predetermined time after a biological fluid is applied to the strip. The strip measures the concentration of an analyte in the fluid. The timer is a dry coating of an indicator, an enzyme-containing reagent that when hydrated can react with glucose to change the color of the indicator, an inhibitor to inhibit the change in color of the indicator, glucose, and optionally, an aldose that does not react with the enzyme in the reagent. Preferably, the reagent and glucose are present in excess in the coating, and the time it takes for the timer color to change can be controlled by the inhibitor concentration. The aldose provides timer stability, probably by interfering with glycosylation by the glucose in the dry state.

23 Claims, 2 Drawing Sheets

FIG. 2
FIG. 3
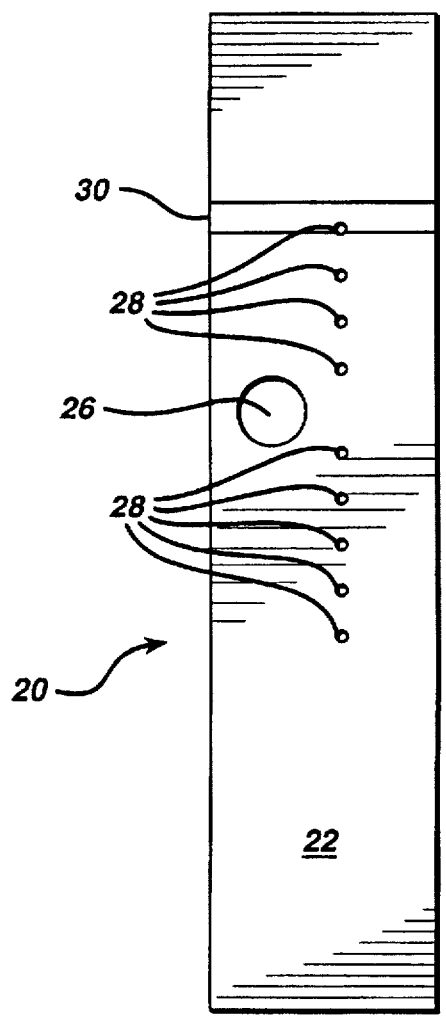
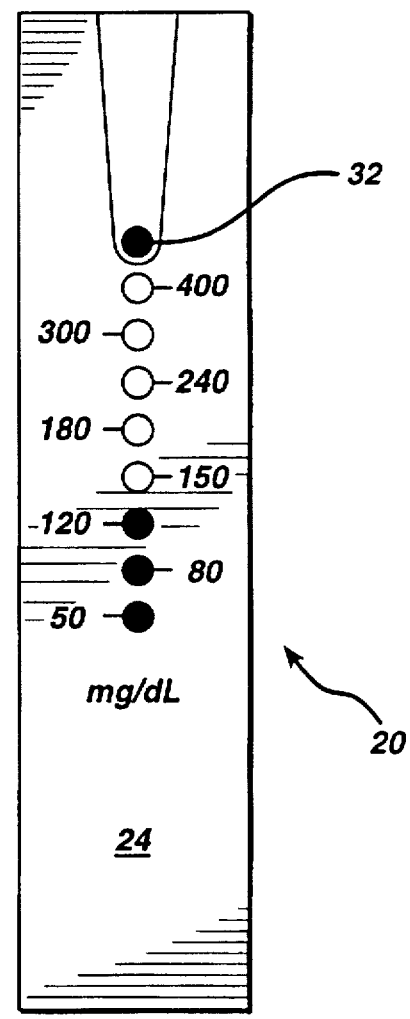

CHEMICAL TIMER FOR A VISUAL TEST STRIP

CROSS-REFERENCE TO RELATED APPLICATIONS

This application is a continuation-in-part of U.S. application Ser. No. 411,238, filed Mar. 27, 1995 now abandoned.

BACKGROUND OF THE INVENTION

1. Field of the Invention

This invention relates to a device that chemically determines a time interval; more particularly, an interval during which a test strip measures the concentration of an analyte in a biological solution.

2. Description of the Related Art

Many visual test devices have been developed for measuring the concentration of certain analytes in biological solutions. These devices have, for example, measured glucose, cholesterol, proteins, ketones, phenylalanine, or enzymes in blood, urine, or saliva.

Dry phase reagent strips incorporating enzyme-based compositions are used extensively in clinical laboratories, physician's offices, hospitals, and homes to test samples of biological fluids for glucose concentration. In fact, reagent strips have become an everyday necessity for many of the nation's several million diabetics. Since diabetes can cause dangerous anomalies in blood chemistry, it can contribute to vision loss, kidney failure, and other serious medical consequences. To minimize the risk of these consequences, most diabetics must test themselves periodically, then adjust their glucose concentration accordingly, for instance, through diet control and/or with insulin injections. Some patients must test their blood glucose concentration as often as four times daily or more.

It is especially important for diabetics who must control their diet in order to regulate sugar intake and/or administer insulin injections, and who must be guided in this regard by frequent tests of blood glucose concentration, to have rapid, inexpensive, and accurate reagent strips for glucose determination.

Reagent strips are known that contain an indicator which turns a different shade of color, depending on the concentration of glucose in a biological fluid that has been applied to the strip. Although some of these strips use reduction chemistries, more commonly they involve an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide. (See, for example, U.S. Pat. No. 5,306,623.)

U.S. Pat. No. 3,964,871, issued Jun. 22, 1976, to Hochstrasser, discloses a disposable indicator strip for directly measuring substances, such as glucose, in biological fluids. The indicator registers the concentration of the substance by including both an indicator reagent, which is oxidized and changes color when it reacts with the substance, and an "antagonist" that in some way prevents the accumulation of oxidized indicator until it has been completely consumed.

Palmer et al. disclose a "digital" quantitative assay system for glucose and other analytes in European Patent Application Publication No. 0 317 070, published May 24, 1989 (see also U.S. Pat. No. 5,036,000, issued Jul. 30, 1991). That system measures the concentration of an organic compound in a biological fluid by first oxidizing the compound with a substrate-specific oxidase enzyme to produce hydrogen peroxide. The system includes a chromogen that is a reductant of hydrogen peroxide and an air-stable hydrogen peroxide reductant that has a larger reduction potential. The larger reduction potential delays any detectable color change by the chromogen until the air-stable first hydrogen peroxide reductant has been consumed. Thus no color change results if the hydrogen peroxide to be measured is less than a pre-determined level corresponding to the concentration of the air-stable peroxide reductant. As a result, the system measures the concentration quantitatively, independent of color change intensity.

Ismail et al, U.S. Pat. No. 4,649,122, issued Mar. 10, 1987, disclose a viability test device that confirms the viability of a test composition for determining the concentration of an analyte. The viability is measured by wetting the device. When wetted with water, the test changes color or undergoes some other change to confirm to the user that the strip is viable.

White-Stevens and Stover, Clin. Chem. 28, 4, 589–595 (1982), discuss interference that can be caused by ascorbic acid on diagnostic tests. The ascorbic acid causes a lag time in color development of tests based on the use of peroxidase and redox indicators.

Whether the test is conducted in the home, physician's office, clinic or a hospital, accuracy and reproducibility of the glucose determination are extremely important. In the case of a color-indicating reagent strip, it is desirable that the color change be pronounced and insensitive to variations in compounds contained in the biological fluid other than glucose. In the case of a visually-read reagent strip, it is especially important that diabetics, who may be suffering from impaired vision, have a test reagent that exhibits a significant color change dependent upon glucose concentration, although color change as exhibited by a change in absorbance at a given wavelength is also important for the accuracy of meter-read strips.

Since the color change involves a series of chemical reactions, it doesn't happen instantaneously. Thus, the user must wait a period of time—typically a minute or less—for the reactions to take place. When a meter reads the strip, timer circuitry can give a signal that indicates the reactions are completed. However, when a strip is read visually, without a meter, the user may underestimate the time needed, read the strip prematurely, and get an incorrect result. Alternatively, the user may feel the need to wait an excessive time before reading the strip, to be sure the reaction is complete, causing unnecessary delay and user dissatisfaction. There is thus a need for a "chemical" timer; i.e., an element on the strip that will change color regardless of the concentration of glucose (or other analyte of interest) in the sample, but will do so only after sufficient time has passed to complete the color-forming reactions with the sample.

SUMMARY OF THE INVENTION

In accordance with the present invention, a chemical timer for a visual test strip for measuring the concentration of an analyte in a biological fluid enables a user of the test strip to be sure that he or she has waited long enough to get a proper reading, without requiring the user to wait an inordinately long time. The timer comprises a dry coating of a) a colored indicator composition;

b) an enzyme-containing reagent that, when hydrated, is capable of reacting with glucose to change the color of the indicator, c) an inhibitor to inhibit the change in color of the indicator;

d) glucose, and e) an aldose that does not react substantially with the enzyme in the reagent, in which the inhibitor and glucose concentrations in the dry coating are selected so that the glucose, over a predetermined time after the biological fluid sample is applied to the strip, reacts with the reagent to change the color of the indicator. By referring to the indicator as "colored", we do not mean to imply that it is not white; in fact in a preferred embodiment, white is the color of the indicator before hydration.

In another embodiment of this invention, a method for preparing a chemical timer for a visual test strip for measuring the concentration of an analyte in a biological fluid that is applied to the strip comprises the steps of a) coating onto a porous membrane a solution of an enzyme-containing reagent that, when hydrated, is capable of reacting with glucose to form a reaction product;

b) drying the coating to form a first layer, and c) applying onto the first layer a second layer that contains
  (i) an indicator that can react with the reaction product to cause a color change,
  (ii) an inhibitor to inhibit the change in color of the indicator,
  (iii) glucose, and
  (iv) an aldose that does not react substantially with the enzyme in the reagent.

The phrase "not react substantially with the enzyme in the reagent," when used in this specification and claims, means reacting relatively much less with the enzyme than does glucose; i.e., less than about 10% of the glucose reactivity.

The strip is of the type that provides a visible indication of the concentration of an analyte that is contained in a biological fluid applied to a "sample side" of the strip. The visible indication appears on the opposite (or "testing") side of the strip. There is generally a delay between the time when the fluid sample is applied to the sample side and when a corresponding visible indication—typically, a color change—appears on the testing side. Therefore, unless the user waits for at least a minimum length of time before taking a reading, the reading may give an incorrect value. Furthermore, the appropriate minimum delay time can be affected by changes in the environment or the strip chemistry, for example ambient temperature or aging effects. The chemical timer of the present invention provides to the user a visible indication when enough time has elapsed from the time that a fluid sample was applied to the strip.

The chemical composition of the test strip depends, of course, on the analyte/biological fluid to be measured. Test strips can be designed to detect analytes such as glucose or other sugars, alcohol, cholesterol, proteins, ketones, uric acid, phenylalanine, or enzymes in biological fluids such as blood, urine, and saliva, as well as water. A chemical timer for a reagent test strip would generally be, but need not be, adapted to respond to the same analyte/biological fluid combination as the reagent test strip itself. For example, if a test strip were designed for measuring alcohol in whole blood, it may not be practical to load a chemical timer with alcohol and an inhibitor for a color-forming reaction between the alcohol and the reagent in the strip. In that case, the timer could include glucose, a reagent for reacting with glucose to form a distinguishable color, and an inhibitor for that reaction. When blood is added to the strip, the timer will be hydrated and change color after a time delay whose duration depends on the inhibitor concentration. Of course, for a "glucose timer" to be suitable for use on an "alcohol strip", it is essential that the time for the glucose reaction can be adjusted to that which is appropriate for the alcohol strip. For the sake of convenience and brevity, the timer and reagent test strips disclosed in the most detail in this specification detect glucose in blood. A person of ordinary skill in the art could readily adapt the information in this disclosure for detecting other analyte/biological fluid combinations.

An indicator strip of the present invention provides a relatively simple and rapid determination of glucose concentration in blood. The strip comprises a porous matrix having a sample side and a testing side. The matrix is generally a membrane and the two terms are used interchangeably in the present specification and the appended claims. A testing reagent is applied to the matrix and, to a greater or lesser extent, is impregnated within the pores of the matrix. For simplicity, we describe the reagent on the matrix as a "coating", in this specification and in the appended claims, recognizing that the reagent coating penetrates the matrix to some extent. The matrix is adapted to accept an unmeasured sample of whole blood, containing red cells and glucose, applied onto the sample side. The porosity of the matrix permits fluid to pass from the sample side toward the testing side, for example by capillary action. Thus, the testing reagent can react with glucose in the blood to cause a color change on or near the testing side. Since the strongly-colored red cells can make it harder to detect the color change, the matrix may have pores with sizes graduated from large pores on the sample side to smaller pores on the testing side, in order to trap red cells away from the testing side. A variety of materials may be used for the various components of the indicator strip and timer of this invention. Some of these materials are disclosed in U.S. Pat. No. 5,306,623, issued Apr. 26, 1994 to Kiser et al., and incorporated herein by reference.

The testing reagent comprises a component for converting glucose to hydrogen peroxide, such as glucose oxidase, and one or more components for detecting the hydrogen peroxide produced from the glucose present in the sample. The components for detecting hydrogen peroxide may be a peroxidase, preferably horseradish peroxidase, together with an "indicator" that changes color in the course of the reaction. The indicator may be an oxidizable dye or a dye couple. The peroxidase catalyzes the oxidation of the indicator in the presence of hydrogen peroxide. The final element of the reagent test strip coating is an inhibitor that retards the color-changing oxidation of the indicator.

In the preferred embodiment, the indicator strip is segmented along its length in such a way that adjacent segments have varying indicator/inhibitor balances. We designate these segments "result segments". A particular result segment only changes color if and when enough glucose is present to first cause all the inhibitor to be used up and to then oxidize the indicator and thereby cause the characteristic color change. Thus, a color change in a particular result segment evidences a threshold glucose concentration in the original blood sample. Along the strip, in a particular direction, each successive result segment has an inhibitor/indicator balance that corresponds to a stepwise increase in threshold glucose concentration. This can be accomplished, for example, if the indicator concentration is the same for all segments and each successive segment has a stepwise greater inhibitor concentration than the preceding one. Clearly, other inhibitor/indicator balances are also possible.

If the result segments have indicator/inhibitor concentrations in the appropriate range for a particular test sample, adjacent segments react with the analyte such that one result segment is colored and an adjacent one is not. That result indicates that the glucose concentration in the sample is at least equal to the threshold concentration required to change the color of the one segment, but not as great as that required to change the color of the adjacent segment. The timer element coating comprises the elements of the indicator strip—a porous matrix having a testing reagent coated on it—and, in addition, glucose. Preferably glucose is present in the timer in an amount well in excess of that required to overcome the inhibitor. In that case, the time required for the color change (after the sample hydrates the timer coating) is longer or shorter depending on whether more or less inhibitor is present. Color changes in the strip and in the timer can be observed either directly by the eye or with an optical instrument that detects changes in reflectance.

Ideally, the reagent chemistry is entirely stable in the dry state and is not activated by the glucose in the timer element coating. As described above, however, the timer is not entirely stable, even when it is maintained in a dry state. Instead, stable compounds are formed between glucose in the timer and low-molecular-weight proteins and also, perhaps, between glucose and enzymes in the coating. To prevent the consumption of glucose by the above glycosylation reactions, a stabilizer may be added. The stabilizer glycosylates more efficiently than does glucose, but does not react with glucose oxidase.

The time required for the timer indication to appear is affected by strip parameters that similarly affect the time required for a visible indication of glucose concentration to appear. Thus, if low ambient temperature or aging of the strip components extends the time needed for a valid measurement of glucose concentration it also extends the time for the chemical timer indication. Finally, if strip mishandling—for example, exposure to moisture—causes the color change that marks completion of the chemical timer reaction to take place before a strip is to be used, the user is alerted to the fact that the strip has been rendered inaccurate and will know not to use it.

BRIEF DESCRIPTION OF THE DRAWINGS

FIG. 2 is a plan view of the testing side of a direct-reading reagent test strip of the present invention.

FIG. 3 is a plan view of the sample side of the strip of FIG. 2.

DETAILED DESCRIPTION OF THE INVENTION

Figure 1:
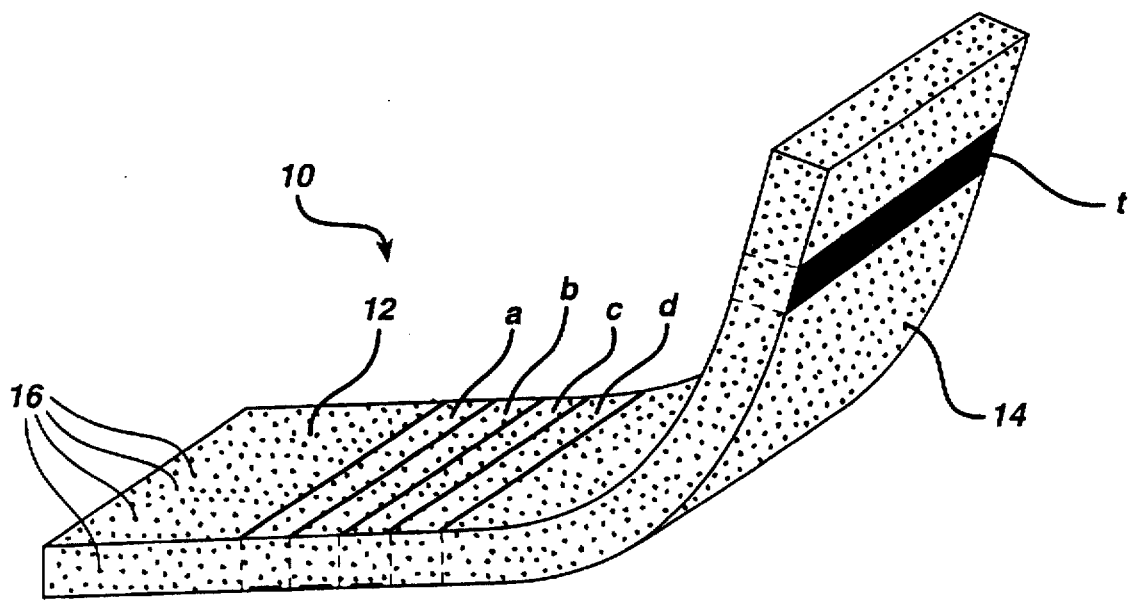
FIG. 1 is a perspective view of the matrix of a direct-reading reagent test strip of the present invention.

A timer of the present invention measures a predetermined time interval chemically. It is particularly adapted for inclusion on a visual test strip for measuring concentration of an analyte in a biological fluid. Such a test strip comprises a porous matrix that incorporates a testing reagent that undergoes a color change in response to the analyte in a biological fluid sample that is applied to the strip.

The matrix may be of a uniform composition or may be a coated substrate and may be either isotropic or anisotropic. It has a sample side, to which the sample is applied, and a testing side, where the color change is observed. Preferably, the matrix is an anisotropic membrane; more preferably, an anisotropic membrane having a large range of pore sizes. For example, a gradient of pore sizes from about 0.1 micrometers to about 150 micrometers may extend through the matrix. At the large-pore end, pore size is more preferably in the range from about 30 micrometers to about 40 micrometers. At the end of the matrix where the pores are smallest, the void volume is relatively small, and the material of the membrane is generally quite dense, within a layer that can constitute up to 10%–20% of the membrane's thickness. Within this layer, pore size is preferably in the range from about 0.1 to about 0.8 micrometers, with a nominal pore size preferably about 0.3 micrometers. When the biological fluid is applied to the sample side, the sample encounters increasingly smaller pores as it penetrates the membrane. Eventually, solids such as red blood cells reach a position in the membrane where they can penetrate no further. The balance of the sample, still containing the dissolved glucose, penetrates through to the testing side. The anisotropic nature of the membrane and/or use of a separating component (discussed below) in the matrix permits relatively rapid flow rates through the membrane, even while filtration of the solids is taking place.

As the sample passes through the matrix, reaction with the reagent causes a light-absorbing dye to be formed or decomposed in the void volume near the testing side, thereby substantially affecting reflectance from the matrix.

Polysulfones and polyamides (nylons) are examples of suitable matrix materials. Other polymers having comparable properties may also be used. The polymers may be modified to introduce other functional groups which provide for charged structures, so that the surfaces of the matrix may be neutral, positive, or negative.

A preferred method of preparing the porous material that forms the matrix is to cast the polymer without a supporting core. Such a matrix is, for example, the anisotropic polysulfone membrane available from Memtec, Inc., Timonium, Md. A matrix of less than about 200 micrometers thickness is usually employed, with about 115 to 155 micrometers being preferred. A thickness of about 130 to 140 micrometers is most preferred, particularly when the matrix is nylon or anisotropic polysulfone. The matrix may optionally be attached to a support in order to give it physical form and rigidity, although this is not essential. Preferably, support is provided by sandwiching the matrix between thermoplastic sheets. The sheet on the sample side includes an opening through which a sample may be introduced. The sheet on the testing side permits the color of the testing side of the matrix to be viewed.

The membrane may be treated with testing reagent by dipping it into an admixture of the components, thereby saturating the membrane matrix. Excess reagent may be removed by mechanical means such as, for example, a doctor blade or glass rod. The membrane is then dried.

The testing reagent comprises (i) a component for converting glucose to hydrogen peroxide, (ii) a component for detecting hydrogen peroxide, and (iii) a component for inhibiting the component that detects the hydrogen peroxide. The reagent may optionally further comprise a separating component which causes solids, such as red blood cells, to become attached to or entrapped in the matrix, effectively removing the solids from the biological fluid. Additional components may also be included as described hereinbelow and in the Examples.

Preferred components for converting glucose to hydrogen peroxide include glucose oxidase, an enzyme that is usually obtained from *Aspergillus niger* or Penicillium. Glucose oxidase reacts with glucose and oxygen to produce gluconolactone and hydrogen peroxide. Optimum glucose oxidase concentration depends on the composition of the indicator system. For example, if the indicator system is MBTHSB- ANS (which is described below), then glucose oxidase in the range from about 500–10,000 U/mL is suitable, more preferably from about 700–2000 U/mL, and most preferably about 1000 U/mL. Generally, higher concentrations of glucose oxidase cause the reaction to proceed more rapidly and inversely.

The hydrogen peroxide so produced reacts with the component for detecting hydrogen peroxide, which comprises a peroxidase that selectively catalyzes a reaction between the hydrogen peroxide and an indicator. The peroxidase uses hydrogen peroxide as an oxidant which is capable of removing hydrogen atoms from various substrates. A suitable peroxidase may contain ferriprotoporphyrin, a red hemin obtained from plants. Peroxidases obtained from animals, for example from the thyroid glands of animals, are also suitable. Horseradish peroxidase (HRPO) is especially preferred as a constituent of the component for detecting hydrogen peroxide.

The hydrogen peroxide, preferably catalyzed by a peroxidase, reacts to either directly or indirectly form or decompose an indicator dye that absorbs light in a predetermined wavelength range. Preferably, the indicator dye absorbs strongly at a wavelength different from that at which the testing reagent absorbs strongly. The oxidized form of the indicator may be the colored, faintly-colored, or colorless final product that evidences a change in color of the testing side of the matrix. That is to say, the testing reagent can indicate the presence of analyte in a sample by a colored area being bleached or, alternatively, by a colorless area developing color.

Indicators that are useful in the present invention include (a) 3-methyl-2-benzothiazolinone hydrazone hydrochloride (MBTH) combined with 3,3-dimethylaminobenzoic acid (DMAB); (b) MBTH combined with 3,5-dichloro-2-hydroxybenzene-sulfonic acid (DCHBS); (c) 4-aminoantipyrene (4-AAP) and 5-oxo-1-(p-sulfophenyl)-2-pyrazoline-3-carboxylic acid (OPSP); (d) 4-AAP and N-(m-tolyl)-diethanolamine (NDA); (e) 2,2'-azino-di (3-ethylbenzthiazoline) sulfonic acid (ABTS); (f) 4-AAP and 4-methoxynaphthol; (g) pyrogallol red (PGR); (h) bromopyrogallol red (BPR); (i) acid green 25 (AG); or (j) [3-methyl-2-benzothiazolinone hydrazone]N-sulfonyl benzenesulfonate monosodium (MBTHSB), combined with 8-anilino-1-naphthalene sulfonic acid ammonium (ANS). MBTHSB-ANS is preferred. Additional information regarding MBTHSB-ANS appears in copending PCT Application Ser. No. US95/12091, filed on Sep. 7, 1995 and incorporated herein by reference.

The inhibiting component retards the reaction between the hydrogen peroxide and the dye or dye precursor, for example by reducing the hydrogen peroxide or by reducing the oxidized dye. In principle there are two different modes of operation for an inhibitor. First, the inhibitor could compete with the indicator and thereby slow the rate at which the color change takes place in the indicator. Alternatively, the inhibitor could be non-competitive, so that substantially all the inhibitor is consumed before any substantial color change takes place in the indicator. Preferably, inhibitors of the present invention operate by the latter mechanism.

Among the range of suitable inhibitors are 2,3,4-trihydroxybenzoic acid; propyl gallate; 3,4 dihydroxy cinnamic acid; 3,4 dihydroxy benzaldehyde; gallic acid; 5,6-diaminouracil; ascorbic acid; and isoascorbic acid. Ascorbic acid is preferred; however, ascorbic acid oxidizes in aqueous solution. To reduce oxidation, other solvents can be used. Preferred solvents are primary alcohols, such as ethyl, methyl, or isopropyl alcohol. Ethyl alcohol is preferred, particularly concentrated solutions; i.e., solutions of 50% or more ethanol.

Although the anisotropic membrane that is the preferred matrix filters out red blood cells and holds them away from the testing side, optionally the testing reagent may also contain a separating component. The separating component should be capable of producing a relatively clear colorless fluid from fluid containing red blood cells, e.g., whole blood, by sequestering red blood cells in the matrix. Separating components for use in the instant invention include but are not limited to polyethylene glycol, poly(methylvinyl ether/maleic)anhydride, polypropylene glycol, polystyrene sulfonic acid, polyacrylic acid, polyvinyl alcohol, and polyvinyl sulfonic acid at a pH of between about 4.0–8.0. Such separating components are present in the matrix in amounts that will vary depending upon their charge and molecular weight, the other components imbedded in the matrix, the matrix pH and pore size, and the residual moisture of the matrix after drying. Such parameters are readily determinable by one skilled in the art. For example, when polypropylene glycol is employed as the separating component, (e.g., PPG-410 from BASF, Wyandotte, Mich.), it is preferably present at about 2–30% weight to volume (w/v), and more preferably 8–10% w/v. Other separating components can also be employed in a concentration of about 2–30% w/v. The polymeric separating components may be impregnated or imbedded in the matrix. Some water soluble salts can also effect such a separation. Among salts suitable for separating blood components are citrates, formates, and sulfates, as well as certain acids, such as amino acids, citric acid, phytic acid, and malic acid. (See, e.g., U.S. Pat. No. 3,552,928, issued Jan. 5, 1971, to M. C. Fetter.) An advantage of including the separating component is that with solids such as red blood cells substantially removed from the biological fluid, there is less background color at the test site to obscure a change in coloration produced by the testing reagent.

Other components may be imbedded into the matrix to enhance the coloration and readability of the reagent strips and to preserve the uniformity and integrity of the matrix. For example, the testing reagent may include salts and/or buffers to aid in the separation of the dye in the matrix. Such buffers may contain for example, citric acid, present in solution at from about 0.01M to about 1.0M, and preferably at about 0.1M. Other acidic buffers may also be employed.

Compounds that make the matrix hydrophilic or compounds that can act as stabilizers, such as hydrolyzed proteins, may also be employed. Such compounds include but are not limited to for example bovine serum albumin, polypeptides and the low molecular weight protein available as CROTEIN SPA (CRODA, Inc. New York, N.Y.). Such compounds are used at concentrations of for example about 1.0 mg/mL to about 100.0 mg/mL. In the case of CROTEIN, about 20 mg/mL is preferred.

Other stabilizers and preservatives may also be included in the coating for the matrix. For example ethylene diamine tetraacetic acid (EDTA), diethylene triamine pentaacetic acid (DTPA) and related compounds may be employed, for example, at concentrations of about 0.01 mg/mL to about 10.0 mg/mL. Among the purposes of the preservatives is to help to stabilize the inhibitor.

Some of the indicators (e.g., BPR) have an undesirable tendency to migrate in the matrix. When such an indicator is used, an ion pairing agent is included to prevent such migration. For example, the polyethylene glycol derivatives commercially available as POLYQUART (H) (Henkel, Inc., Ambler, Pa.) are particularly useful for their ability to facilitate ion pairing between the indicator and other matrix substituents.

When the presence of an analyte is indicated by color formation (e.g., MBTHSB-ANS), surfactants may be added to brighten the color and enhance the contrast with the surround.

Organic solvents may also be employed in the practice of this invention and may be included in the formulation of the testing reagent for the matrix, provided, of course, that they are compatible with the matrix and testing reagent compositions. Potentially suitable organic solvents include chloroform, acetone, alcohols, methylene chloride, diethyl and petroleum ethers, acetonitriles, and mixtures thereof. In the practice of the present invention, 70% ethanol in water is particularly preferred.

The testing reagent that is coated on or impregnated into the matrix is not uniform over the surface of the test strip. Instead, the reagent is preferably applied to the matrix in a series of parallel stripes, or "result segments", in which the composition in adjoining result segments increases, stepwise, in inhibitor concentration. Thus each succeeding segment requires, stepwise, a greater glucose concentration in the sample to cause the segment to change color.

The timer segment of the matrix is coated or impregnated with a composition that consists of the testing reagent and, in addition, glucose and an aldose that does not react with the enzyme in the reagent. The glucose is added so that the timer segment will change color, over time, when it is hydrated by the addition of an aqueous sample to the strip. The aldose is added to stabilize the timer segment. While we do not wish to be bound by any particular theory, we believe that the need for the aldose arises from the fact that many monosaccharides form stable covalent complexes with the amino groups of proteins. Thus, some of the glucose in the timer could react with the low-molecular-weight proteins and, perhaps, with enzymes in the testing reagent to form complexes. This process ("glycosylation")proceeds non-enzymatically in two steps. The first step, which is readily reversible, is the formation of a Schiff's base; an aldimine in the case of aldose sugars. Over time this shifts to a ketoamine form, which is highly stable, in an irreversible reaction.

To prevent the consumption of glucose in the glycosylation process, which we believe occurs in the timer, we use as a stabilizer a sugar which is a more efficient glycoslator and which competes successfully with glucose for the amino groups of the proteins. For obvious reasons, it is also necessary to use a sugar which does not react with glucose oxidase.

Bunn and Higgins, Science 213, 222 (10. Jul. 1981), found that the glycosylating efficiency of monosaccharides is related to the proportion of the sugar in solution which is in the straight-chain aldehyde configuration. Table 1, adapted from their paper, gives a list of rates of reactivity with hemoglobin, k, of a number of aldoses, all of which are non-reactive with glucose oxidase. In principle, the k value should be as high as possible and, in any case, higher than that of glucose. In practice, the stabilizer must react more readily than glucose with the moieties that would otherwise react with and deplete the glucose. Thus, enough stabilizer should be present to react with all these moieties (i.e., stabilizer at least equimolar with the moieties.) Preferably, excess stabilizer is added, particularly if its k is only slightly higher than that for glucose. In that case, there is no appreciable glucose depletion. By the above criterion, mannose and galactose have been determined to be suitable stabilizers. Because they are inexpensive and readily available, they are preferred.

TABLE 1

| Aldose | Reactivity Rate (k) |
|---|---|
| D-Glucose | 0.60 |
| D-Mannose | 3.2 |
| 6-Deoxy-L-mannose (fucose) | 0.7 |
| D-Allose | 1.4 |
| D-Galactose | 2.8 |
| D-Xylose | 2.9 |
| D-Talose | 5.2 |
| D-Altrose | 5.0 |
| D-Ribose | 10.0 |
| D-Idose | 55 |
| 5,6-Di-O-methyl-D-glucose | 104 |

The testing reagent's purpose is to change color in response to glucose. Thus, combining the glucose and the reagent in the timer without causing the color change requires some care. An amount of inhibitor beyond that required for the timing function must be present to compensate for this effect. The rate at which the timer segment is dried, after the glucose containing solution is applied, is controlled. In practice, the membrane is first coated with a solution containing buffers and enzymes, and that coating is dried to form a first layer. Then, a second coating pass applies a solution containing indicator, inhibitor, glucose, and an aldose to form a second layer. Parameters such as web speed, oven temperature and airflow, and quantity of coating solutions deposited will have been fixed beforehand and appropriate adjustments made to the inhibitor and/or glucose concentrations. Instead of the second layer being applied as a coating, an alternative, less preferred, involves making the second coating on a separate web and then laminating it over the first layer.

When a sample is applied to the strip, hydration of the timer segment composition permits the color-forming reaction to proceed. The time it takes for the timer segment to change color is then determined by the temperature and by characteristics of the testing reagent, particularly the inhibitor concentration, the amount of glucose, and the hydration and oxygen diffusion rates.

The timer color-change time can be made to depend on the glucose concentration in the sample or, alternatively, to be independent of that concentration. By incorporating a great excess of glucose in the timer, the time is substantially independent of the sample's glucose concentration. By incorporating less glucose in the timer, the time may be made to depend on the glucose in the sample; i.e., the timer will change color faster if glucose concentration in the sample is greater. Preferably, the glucose concentration in the timer coating solution is greater than about 1500 mg/dL, which makes the timer substantially independent of the sample glucose concentration in the desired range from about 40–400 mg/dL as well as outside that range. The timer composition should then include at least as much, or more, inhibitor than does the result segment that has the highest inhibitor concentration (which corresponds to the highest glucose reading).

The timer also serves an important quality-control function, by making it apparent when a test strip has been contaminated by exposure to moisture. The test strip must remain dry until the time it is to be used, because components that convert glucose to hydrogen peroxide (generally enzymes) tend to degrade on exposure to moisture. Thus, if the strip is prematurely exposed to moisture, it will become unreliable. But the unreliability of the test strip is not apparent to a user, who may, therefore, use such a strip and get an erroneous result. However, if the strip includes a timer segment, exposure to moisture causes the timer to change color, which alerts the user to that fact that the strip is compromised.

The invention will now be described further with reference to the Figures. FIG. 1 shows a matrix 10 of the present invention, for measuring the amount of analyte in a biological fluid. Although shown in an arched position, matrix 10 is flexible and is generally in a flat plane when used. The matrix includes a sample side 12, to which the biological fluid sample is applied, and a testing side 14, on or near which a change in color indicates the presence of the analyte. The color change results from the interaction of the analyte with reagent impregnated in pores 16. Preferably, for measuring the concentration of glucose in blood, pore sizes are relatively large near sample side 12 and decrease in size as testing side 14 is approached. The pore size gradient serves to trap red blood cells near sample side 12, so that their color does not interfere with the ability to see the color change that indicates the presence of the analyte.

Four result segments, a, b, c, and d are shown schematically. Each succeeding segment has stepwise more inhibitor than the one before. Thus, for example, if a sample causes segments a, b, and c to change color, while d does not (as shown in FIG. 1), it means that the glucose concentration in that sample is at least as great as that needed to consume the inhibitor level of segment c, but not enough to overcome the inhibitor in segment d. Once the result segments are calibrated, that result yields a quantitative measure of the glucose concentration. Segment t, the timer, incorporates a high concentration of glucose, in addition to the testing reagent impregnated in the result segments. The inhibitor in segment t is at least as great as in the result segments, and the time required to consume the inhibitor in segment t is at least as great as that required to consume the inhibitor in the other segments. Thus, when segment t undergoes a color change (as shown in FIG. 1), enough time has elapsed to cause the color change in all the result segments whose inhibitor concentration is low enough to be consumed by the glucose concentration in the sample, and a correct measurement can be made without further delay.

In an actual test strip, the membrane matrix of FIG. 1 is sandwiched between two cover sheets, which may be of any suitable thermoplastic film, well known in the art. FIGS. 2 and 3 are plan views of the sample side 22 and testing side 24 of a test strip 20, respectively. In use, a blood sample is applied to opening 26 on sample side 22. The sample spreads by capillary action longitudinally toward the top and bottom of the strip and permeates the matrix toward testing side 24. Optional vent holes 28 facilitate the spread of sample along the strip. The appearance of sample through optional clear window 30 confirms that sufficient sample has been provided for a measurement. Indicator circles on testing side 24 admit oxygen needed for the color-forming reaction and are labeled to show the blood glucose concentration. As the test progresses, indicator circles on testing side 24 change color sequentially if the blood glucose concentration in the sample meets or exceeds the amount that corresponds to that circle. Thus, the result depicted in FIG. 3 indicates that the sample glucose concentration is at least 120 mg/dL, but less than 150 mg/dL. The reading can be taken at any time after timer circle 32 changes color. Note that in the FIGS. the color change caused by the reaction with glucose is from white to colored. However, the system could alternatively operate with an indicator dye that is destroyed by the glucose-induced oxidation, with a corresponding color change from colored to white.

For a better understanding of the present invention, the following Examples further illustrate various embodiments of the invention. The Examples are not intended to be in any way limiting.

EXAMPLE 1

BPR Indicator

The following solution was prepared:

|  |  | Enzyme Solution |  |
|---|---|---|---|
| Distilled Water | 83.5 g | 0.2M Aconitic Acid | 27.0 g |
| 1% (w/w) EDTA Na$_2$ | 23.8 g | Glucose Oxidase | 165,000 U |
| Aconitic Acid | 6.0 g | HRPO | 340,000 U |
| NaOH (solid) | 2.2 g |  |  |
| CROTEIN SPA | 4.2 g |  |  |
| Imidazole | 0.6 g |  |  |
| Mannitol | 3.0 g |  |  |
| 5% (w/w) SURFACTOL Q1 | 3.0 g |  |  |
| Adjust pH to 4.80 |  |  |  |
| Ethyl Alcohol | 40.0 g |  |  |
| PPG-410 | 5.6 g |  |  |
| Enzyme Solution | 28.0 g |  |  |

Memtec BTSH 55 membrane was immersion coated in this solution and the excess doctored off with glass rods. The coated membrane was dried in a flotation dryer at 180 F. under moderate airflows so that the web was substantially dry within 20 seconds. The web was spooled in preparation for the second coating, described below.

The following solutions were prepared:

| Ascorbate (inhibitor) stock solution |  | Diluent |
|---|---|---|
| Distilled Water | 190 g | 370 g |
| 1% EDTA Na$_2$ | 55 g | 107 g |
| BPR | 0.36 g | 0.71 g |
| POLYQUART ® H | 6 g | 11.8 g |
| PPG-410 | 14.2 g | 27.8 g |
| Ascorbic Acid | 1.37 g | — |
| Ethyl Alcohol | 243 g | 477 g |

| Timer Solution |  |
|---|---|
| Diluent (per above formula) | 120 g |
| Ascorbic Acid | 0.885 g |
| Glucose Solution* | 17.25 g |

*The Glucose Solution is a 16,000 mg/dL solution of glucose in water allowed to mutarotate for 24 hours, stored refrigerated.

The following dilutions of the stock solution were made: 0.0405:1, 0.108:1, 0.236:1, 0.369:1, 0.569:1, 1.260:1. This stepwise increase in inhibitor concentration corresponds to the stepwise-greater glucose concentration that the result circles report. These solutions, along with the timer solution, were coated side-by-side onto the large-pore side of the enzyme-loaded membrane so as to deposit approximately $1 \times 10^{-4}$ mL per square millimeter of membrane. The membrane was wet approximately fifteen seconds before experiencing the same drying conditions as described above for the enzyme coating step. Results showed the timer reacting in about 70 seconds with about 95% of results falling between 64 and 79 seconds.

EXAMPLE 2

MBTHSB-ANS Indicator

The following solution was prepared:

| | |
|---|---|
| HPLC water | 1500 mL |
| Citric Acid | 16.92 g |
| Sodium Citrate | 29.88 g |
| Mannitol | 15 g |
| Disodium EDTA | 1.26 g |
| GANTREZ S95 | 6.75 g |
| Crotein SPA | 36 g |
| Glucose Oxidase | 1.69 MU |
| HRPO | 1.5 MU |
| CARBOPOL 910* | 75 mL |
| Disodium Citrate** | 225 mL |

*11% solution in Acetonitrile
**0.1M, pH 5.0

Memtec BTS 30 membrane was coated in a trough so that the large-pored surface contacted the coating solution; excess solution was removed with glass rods as before. The membrane was dried and spooled as in Example 1.

The following solutions were made:

| Solution A (Indicator) | | Solution B (Wetting Agent) | |
|---|---|---|---|
| 70% (v/v) Ethanol | 2819 mL | MAPHOS® 60A | 41 g |
| MBTHSB | 2.98 g | 70% (v/v) Ethanol | 205 mL |
| (NH$_4$) ANS | 25.83 g | | |
| Solution B | 205 mL | | |
| 2% DTPA | 51.25 mL | | |

| Solution C (Ascorbate Stock) | | Solution D (Timer) | |
|---|---|---|---|
| Water | 115 mL | Water | 53 mL |
| Ascorbic Acid | 4.58 g | Ascorbic Acid | 8.75 g |
| Ethanol | 267 mL | Ethanol | 123 mL |
| | | Bring volume to 175 mL with 70% EtOH | |
| | | Glucose Solution | 40.5 mL |

For each inhibitor solution, the volume of Solution A was fixed at 263 mL. For the various result circles, the ratio of 70% EtOH:Solution C was varied from 58.9 to 0.200 so that the volume of 70% EtOH+Solution C added to Solution A was 87.5 mL for all inhibitor solutions. This effectively altered only the concentration of inhibitor in each solution. The solutions containing the stepwise-increasing inhibitor concentration and the timer solution (Solution D) were coated side-by-side onto the large-pore side of the membrane. Deposition rate was adjusted to achieve ~8×10$^{-5}$ mL of inhibitor per square millimeter of membrane. The membrane was dried as above, except that the delay between coating and drying was about 1.6 minutes. Results showed the timer reacting in about 60 seconds with little effect from blood hematocrit from 30 to 55% or glucose from 78 to 420 mg/dL.

EXAMPLE 3

Enhanced Timer Stability

An anisotropic polysulfone membrane, Memtec BTS-30, was coated with Reagent A. The resulting membrane was dried in an air circulating oven maintained at 56° C. for 10 minutes. The membrane was then coated over with Reagent B and was dried at the above conditions. The membrane was then fashioned into strips for testing.

| Reagent A | |
|---|---|
| | wt. (g) |
| Water | 3963 |
| Citric acid | 45.12 |
| Trisodium citrate | 55.68 |
| Mannitol | 40 |
| EDTA | 3.36 |
| GANTREZ S95 | 18 |
| CROTEIN SPA | 57.72 |
| Glucose oxidase (126 U/mg) | 37.6 |
| Horseradish peroxidase (410 U/mg) | 12.25 |
| CARBOPOL 910 in MeCN (0.55 mg/5 mL) | 177.18 |
| 0.1M disodium citrate | 598.3 |

| Reagent B | |
|---|---|
| Dye solution: | |
| Ethanol | 22.5 mL |
| Water | 2.5 mL |
| MBTHSB | 36.3 mg |
| (NH$_4$) ANS | 472.5 mg |

Glucose solutions:

(1) 16,000 mg/dL D-Glucose solution in water
(2) 16,000 mg/dL D-Glucose + 16,000 mg/dL Galactose solution in water
(3) 16,000 mg/dL D-Glucose + 16,000 mg/dL Ribose solution in water
(4) 16,000 mg/dL D-Glucose + 16,000 mg/dL Mannose solution in water

| | Glucose (Control) | Glucose + Galactose | Glucose + Ribose | Glucose + Mannose |
|---|---|---|---|---|
| Dye solution | 5 mL | 5 mL | 5 mL | 5 mL |
| Ethanol | 4.5 mL | 4.5 mL | 4.5 mL | 4.5 mL |
| Water | 0.06 mL | 0.06 mL | 0.06 mL | 0.06 mL |
| solution (1) | 0.44 mL | — | — | — |
| solution (2) | — | 0.44 mL | — | — |
| solution (3) | — | — | 0.44 mL | — |
| solution (4) | — | — | — | 0.44 mL |
| Ascorbic acid | 40 mg | 40 mg | 40 mg | 40 mg |

Strips of all four compositions were divided into two groups for storage:

one group was stored for seven days at 56° C.—accelerated aging the other group was stored for seven days at 5° C.—control At the end of the seven days, the strips were tested with whole blood that contained 100 mg/dL of glucose, 42.5% hematocrit.

The "aged" strips that contained only glucose showed a much longer time to develop full color ("Reaction Endtime") than did the "fresh" (i.e., stored at 5° C.) strips. The strips that included aldose showed significantly less reaction endtime extension.

Table 2 displays the results.

TABLE 2

| Sugar | Difference in Reaction Endtime (56° vs. 5° C.) |
|---|---|
| Glucose (control) | 28 seconds |
| Galactose/Glucose | 16 seconds |
| Ribose/Glucose | 14 seconds |
| Mannose/Glucose | 12 seconds |

In the specification and Examples above, the following trademarks appear:

CARBOPOL 910 polyacrylic acid polymer (B. F. Goodrich)

CROTEIN SPA hydrolyzed collagen—4000 MW (Croda Inc.)

GANTREZ 595 poly (methyl vinyl ether/maleic acid) (International Specialty Products)

MAPHOS 60A complex organic phosphate esters (PPG Industries)

POLYQUART H polyethyleneglycol—15 tallow polyamine (Henkel Canada Ltd.)

SURFACTOL Q1 ethoxylated castor oil (CasChem, Inc.)

It will be understood by those skilled in the art that the foregoing description and Examples are illustrative of practicing the present invention but are in no way limiting. Variations of the detail presented herein may be made without departing from the scope and spirit of the present invention.

We claim:

1. A chemical timer for a visual-reading reagent test strip for measuring the concentration of glucose in a biological fluid that is applied to the strip, the timer comprising a dry coating of
   a) a colored indicator composition,
   b) a reagent that, when hydrated, reacts with glucose to change the color of the indicator,
   c) an inhibitor to inhibit the change in color of the indicator, and
   d) glucose,
in which the inhibitor and glucose concentrations in the dry coating are selected so that the glucose, over a predetermined time after the biological fluid is applied to the strip, reacts with the reagent to change the color of the indicator.

2. The timer of claim 1 in which the biological fluid is blood.

3. The timer of claim 1 in which the indicator is selected from the group consisting of (a) 3-methyl-2-benzothiazolinone hydrazone hydrochloride (MBTH) combined with 3,3-dimethylaminobenzoic acid (DMAB); (b) MBTH combined with 3,5-dichloro-2-hydroxybenzenesulfonic acid (DCHBS); (c) 4-aminoantipyrene (4-AAP) and 5-oxo-1-(p-sulfophenyl)-2-pyrazoline-3-carboxylic acid (OPSP); (d) 4-AAP and N-(m-tolyl)-diethanolamine (NDA); (e) 2,2'-azino-di(3-ethylbenzthiazoline)sulfonic acid (ABTS); (f) 4-AAP and 4-methoxynaphthol; (g) pyrogallol red (PGR); (h) bromopyrogallol red (BPR); (i) acid green 25 (AG); or (j) [3-methyl-2-benzothiazolinone hydrazone]N-sulfonyl benzenesulfonate monosodium (MBTHSB), combined with 8-anilino-1-naphthalene sulfonic acid ammonium (ANS).

4. The timer of claim 3 in which the dye is MBTHSB-ANS.

5. The timer of claim 1 in which the reagent comprises an oxidase enzyme.

6. The timer of claim 5 in which the oxidase enzyme is glucose oxidase.

7. The timer of claim 1 in which the inhibitor comprises ascorbic acid.

8. A visual-reading reagent test strip for measuring concentration of glucose in a biological fluid that is applied to a strip, comprising the chemical timer of claim 1.

9. A method for preparing a chemical timer for a visual-reading reagent test strip for measuring the concentration of glucose in a biological fluid that is applied to the strip, comprising the steps of
   a) coating onto a porous membrane a solution of a reagent that, when hydrated, reacts with glucose to form a reaction product,
   b) drying the coating to form a first layer
   c) applying onto the first layer a second layer that contains
      (i) glucose,
      (ii) an indicator that reacts with the reaction product to cause a color change, and
      (iii) an inhibitor to inhibit the change in color of the indicator.

10. The method of claim 9 in which the reagent comprises glucose oxidase.

11. A method for measuring the concentration of glucose in a biological fluid comprising the steps of
    (a) applying the fluid to a test strip that comprises
       (i) a plurality of result segments that each change color when contacted with fluid containing at least a predetermined amount of glucose, different from the amount of glucose that causes a change in color of the other segments and
       (ii) a timer segment that changes color after a time whose duration is substantially independent of the amount of glucose in the fluid and
    (b) determining the glucose concentration by observing the result segment that has changed color last when the timer segment changes color.

12. A chemical timer for a visual reading test strip for measuring the concentration of an analyte in a biological fluid that is applied to the strip, the timer comprising a dry coating of
    a) a colored indicator composition
    b) an enzyme-containing reagent that, when hydrated, reacts with an analyte to change the color of the indicator;
    c) an inhibitor to inhibit the change in color of the indicator,
    d) glucose, and
    e) an aldose that does not react substantially with the enzyme in the reagent.

13. The timer of claim 12 in which the aldose is selected from the group consisting of mannose and galactose.

14. The timer of claim 12 in which the analyte is glucose.

15. The timer of claim 12 in which the biological fluid is blood.

16. The timer of claim 12 in which the indicator is selected from the group consisting of (a) 3-methyl-2-benzothiazolinone hydrazone hydrochloride (MBTH) combined with 3,3-dimethylaminobenzoic acid (DMAB); (b) MBTH combined with 3,5-dichloro-2-hydroxybenzenesulfonic acid (DCHBS); (c) 4-aminoantipyrene (4-AAP) and 5-oxo-1-(p-sulfophenyl)-2-pyrazoline-3-carboxylic acid (OPSP); (d) 4-AAP and N-(m-tolyl)-diethanolamine (NDA); (e) 2,2'-azino-di(3-ethylbenzthiazoline) sulfonic acid (ABTS); (f) 4-AAP and 4-methoxynaphthol; (g) pyrogallol red (PGR); (h) bromopyrogallol red (BPR); (i) acid green 25 (AG); or (j) [3-methyl-2-benzothiazolinone hydrazone]N-sulfonyl benzenesulfonate monosodium (MBTHSB), combined with 8-anilino-1-naphthalene sulfonate (ANS).

17. The timer of claim 16 in which the indicator is MBTHSB-ANS.

18. The timer of claim 12 in which the enzyme in the reagent comprises an oxidase enzyme.

19. The timer of claim 18 in which the oxidase enzyme is glucose oxidase.

20. The timer of claim 12 in which the inhibitor comprises ascorbic acid.

21. A visual test strip for measuring concentration of an analyte in a biological fluid that is applied to a strip, comprising the chemical timer of claim 12.

22. A method for preparing a chemical timer for a visual reading test strip for measuring the concentration of an analyte in a biological fluid that is applied to the strip, comprising the steps of
   a) coating onto a porous membrane a solution of an enzyme-containing reagent that, when hydrated, reacts with an analyte to form a reaction product,
   b) drying the coating to form a first layer, and
   c) applying onto the first layer a second layer that contains
      (i) an indicator that reacts with the reaction product to cause a color change,
      (ii) an inhibitor to inhibit the change in color of the indicator,
      (iii) glucose, and
      (iv) an aldose that does not react substantially with the enzyme in the reagent.

23. The method of claim 22 in which the analyte is glucose and the enzyme comprises glucose oxidase.

* * * * *